US009532995B2

(12) United States Patent
Govindarajan

(10) Patent No.: US 9,532,995 B2
(45) Date of Patent: Jan. 3, 2017

(54) METHODS FOR THE TREATMENT OF ENDOMETRIOSIS

(75) Inventor: Mirudhubashini Govindarajan, Tamil Nadu (IN)

(73) Assignee: MISCON TRADING S.A., United Arab Emirates (IN)

(*) Notice: Subject to any disclaimer, the term of this patent is extended or adjusted under 35 U.S.C. 154(b) by 345 days.

(21) Appl. No.: 10/927,822

(22) Filed: Aug. 27, 2004

(65) Prior Publication Data

US 2005/0085453 A1 Apr. 21, 2005

Related U.S. Application Data

(60) Provisional application No. 60/500,217, filed on Sep. 3, 2003, provisional application No. 60/526,355, filed on Dec. 1, 2003.

(51) Int. Cl.
*A61K 31/57* (2006.01)
*A61K 9/00* (2006.01)
*A61K 9/10* (2006.01)

(52) U.S. Cl.
CPC ............. *A61K 31/57* (2013.01); *A61K 9/0034* (2013.01); *A61K 9/0019* (2013.01); *A61K 9/10* (2013.01)

(58) Field of Classification Search
CPC ........ A61K 31/57; A61K 9/0034; A61K 9/10; A61K 9/0019
See application file for complete search history.

(56) References Cited

U.S. PATENT DOCUMENTS

| | | | |
|---|---|---|---|
| 3,089,815 A | 5/1963 | Lieb et al. | |
| 4,038,389 A * | 7/1977 | Lamb et al. | 514/178 |
| 5,362,720 A | 11/1994 | Labrie | |
| 5,434,146 A | 7/1995 | Labrie et al. | |
| 5,543,150 A | 8/1996 | Bologna et al. | |
| 5,993,856 A | 11/1999 | Ragavan et al. | |
| 6,225,298 B1 | 5/2001 | Spicer et al. | |
| 6,265,393 B1 * | 7/2001 | Heinrichs | 514/178 |
| 6,287,602 B1 | 9/2001 | Singh | |
| 6,416,778 B1 * | 7/2002 | Ragavan et al. | 424/430 |
| 6,495,164 B1 * | 12/2002 | Ramstack et al. | 424/489 |
| 6,613,355 B2 * | 9/2003 | Ng et al. | 424/462 |
| 2002/0012703 A1 | 1/2002 | Singh | |
| 2002/0061303 A1 | 5/2002 | Singh | |
| 2002/0072509 A1 * | 6/2002 | Stein et al. | 514/169 |
| 2002/0115645 A1 * | 8/2002 | Colombo et al. | 514/169 |
| 2003/0114430 A1 * | 6/2003 | MacLeod et al. | 514/177 |
| 2004/0105889 A1 | 6/2004 | Ryde et al. | |

FOREIGN PATENT DOCUMENTS

| | | |
|---|---|---|
| EP | 0501056 | 9/1992 |
| EP | 0 785 212 A1 | 7/1997 |
| GB | 784659 | 10/1957 |
| GB | 2252497 A | 8/1992 |
| JP | H04-273822 | 9/1992 |
| JP | H06-508624 | 9/1994 |
| JP | 2000-503980 A | 4/2000 |
| JP | 2001-511773 | 8/2001 |
| NZ | 238542 | 9/1993 |
| RU | 2073534 C1 | 2/1997 |
| WO | WO 95/07699 A1 | 3/1995 |
| WO | 9727210 | 7/1997 |
| WO | WO 98/32422 A1 | 7/1998 |
| WO | WO 00/15766 | 3/2000 |
| WO | 0021511 A | 4/2000 |
| WO | WO 00/21511 | 4/2000 |
| WO | WO 01/87262 A2 | 11/2001 |
| WO | WO 02/28387 | 4/2002 |
| WO | WO 02/067991 A1 | 9/2002 |

OTHER PUBLICATIONS

Schmidt, J.B., Medroxyprogesterone acetate Therapy in Hirsutism, 1985, British Journal of Dermatology, vol. 113, pp. 161-165.*
Orentreich. N. et al., "The Local Antiandrogenic Effect of the Intracutaneous Injection of Progesterone in the Flank Organ of Sexually Mature Male Syrian Golden Hamster", Arch Dermatol Res (1984) 276:401-405.
Official Action dated Dec. 15, 2009; Israel Patent Application No. 174014; 1 page.
First Examination Report dated Nov. 27, 1008; Indian Patent Application No. 1038/DELNP/2006; 2 pages.
Examination Report dated Mar. 11, 2009; New Zealand Patent Application No. 545572; 2 pages.
Examiner's First Report dated Jun. 25, 2009; Australian Patent Application No. 2004267956; 3 pages.
Official Action; Ukraine Patent Application No. 200603518(MI-3954); 2 pages.
Notification of the Second Office Action dated Jun. 19, 2009; Chinese Patent Application No. 200480025218.7; 3 pages.
Official Action; Eurasian Patent Application No. 200600524 (2006030172); 2 pages.
Official Action dated Feb. 28, 2007; Eurasian Patent Application No. 200600524 (2006030172); 4 pages.
Fedele Luigi et al: Use of a levonorgestrel-releasing intrauterine device in the treatment of rectovaginal endometriosis: Fertility and Sterility, vol. 75, No. 3, Mar. 2001, pp. 485-488.
Vercellini Paolo et al: "Comparison of a levonorgestrel-releasing intrauterine device versus expectant management after conversative surgery for symptomatic endometriosis: A pilot study." Fertility and Sterility, vol. 80, No. 2, Aug. 2003, pp. 305-309.
Grigorieva Vera et al: :"Use of a levonorgestrel-releasing intrauterine system to treat bleeding related to uterine leiomyomas." Fertility and Sterility, vol. 79, No. 5, May 2003, pp. 1194-1198.
Affinito P et al: "Endometrial hyperplasia: efficacy of a new treatment with a vaginal cream containing natural micronized progesterone." Maturitas, vol. 20, (1995), pp. 191-198.

(Continued)

*Primary Examiner* — Sue Liu
*Assistant Examiner* — Andriae M Holt
(74) *Attorney, Agent, or Firm* — Finnegan, Henderson, Farabow, Garrett, and Dunner, LLP

(57) ABSTRACT

Endometriosis, including endometriosis externa, endometrioma, adenomyosis, adenomyomas, adenomyotic nodules of the uterosacral ligaments, and endometriotic nodules, such as scar endometriosis are effectively treated by the intralesional administration, including transvaginal, endoscopic or open surgical administration including via laparotomy, of a progestogen. Compositions therefor also are provided.

42 Claims, No Drawings

(56) References Cited

OTHER PUBLICATIONS

Vercellini Paolo et al: "Progestogens for endometriosis: forward to the past." Human Reproducion Update 2003, vol. 9, No. 4,, pp. 387-396.
Simon J A: "Micronized Progesterone: Vaginal and Oral Uses." Clinical Obstetrics and Gynecology, vol. 38, No. 4, Dec. 1, 1995, pp. 902-914.
Lumbiganon Pisake et al: "Protective effect of depo-medroxyprogesterone acetate on surgically treated uterine leiomyomas: a multicentre case-control study." British Journal of Obsetrics and Gynaecology, vol. 103, Sep. 1995, pp. 909-914.
Ikomi A A et al: "Protective effect of depo-medroxprogesterone acetate on surgically treated uterine leiomyomas: a multicentre case-control study." British Journal of Obstetrics and Gynaecology Mar. 1997, vol. 104, No. 3, 1997, pp. 385-386.
Rein M S: "Advances in uterine leiomyoma research: the progesterone hypothesis." Environmental Health Perspectives, vol. 108, Suppl. 5, Oct. 2000, pp. 791-793.
Database Medline [Online], US National Library of Medicine (NLM), Bethesda, MD, US; Dec. 1987 (Dec. 1987), Telimaa S et al: "Placebo-controlled comparison of danazol and high-dose medroxprogesterone acetate in the treatment of endometrosis after conservative surgery,"and Gynecological Endocrinology: The Official Journal of International Society of Gynecological Endocrinology, vol. 1, No. 4, Dec. 1987, pp. 363-371.
Buckett W M et al: "Endometriosis: critical assessment of current therapies." Current Obstetrics and Gynaecology, vol. 8, No. 4, 1998, pp. 204-208.
Supplementary European Search Report dated Jan. 18, 2010 regarding patent application No. EP 04769463.3.
Mexico Application MX2006002486 Office Action Dec. 9, 2010.
Phillipines Application Office Action dated Mar. 16, 2010.
Canada Application 2537702 Office Action dated Mar. 28, 2011.
China Application 200480025218.7 English Translation of Office Action dated Feb. 9, 2011.
Japan Application 2006-525216 English Translation of Office Action dated Mar. 28, 2011.
Merck Manuals, Centennial Edition, 1999, p. 1656-1959 (Cited as 17th Edition, Japanese Version, 1999, p. 1960-1962).
Australia Application AU2004267956 Office Action Jul. 12, 2010.
Australia Application AU2004267958 Office Action Jul. 20, 2009.
Eurasian Application EA200600524 Office Action Apr. 21, 2010.
Eurasian Application EA200600524 Office Action Sep. 27, 2010.
Mexico Application MX2006002486 Office Action Jun. 18, 2010.
Mexico Application MX2006002486 Office Action Oct. 15, 2009.
PCT Application PCTIB04003103 International Search Report mailed Dec. 27, 2005.
PCT Application PCTIB04003103 International Preliminary Report on Patentability and Written Opinion, Jun. 26, 2006.
Coutinho, et al., "Clinical management of leiomyomas with medroxyprogesterone acetate", Progress in the Management of Endometriosis Proceedings of the world congress on endometriosis, XX, XX, Jan. 1, 1995 (Jan. 1, 1995) pp. 421-425, XP002114848.
Europe Application 04769463.3 Office Action dated Apr. 8, 2011.
Indonesia Application W-00200600598 Office Action explanation, dated May 12, 2011.
Korean Application 10-2006-7004304 Office Action translation, dated May 16, 2011.
Abstracts, INDO—US Workshop on Microarray in endometriosis: Clinics to Research Laboratory, Nov. 3-7, 2009. All India Institute of Medical Sciences, pp. 1-11.
Asada et al., "Medical management of endometriosis-associated infertility and endometriosis-associated pain" *Sanfujinka Chiryo*,83(4):443-450 (2001).
CN201010193233.X, Notification of the Second Office Action translation, Mar. 23, 2012.
Donnez, "Endometriosis: enigmatic in the pathogenesis and controversial in its therapy" *Fertility and Sterility*, 98(3):509-510 (2012).
EMD SERONO "Crinone®" Product Monograph. Submission Control No. 143981. Date of Approval: May 2, 2011, 18 pages.
Fraser, "Recognising, understanding and managing endometriosis" *J. Hum. Reprod. Sci.*, 1(2):56-64 (2008).
Hornstein et al., "Prospective randomized double-blind trial of 3 versus 6 months of nafarelin therapy for endometriosis associated pelvic pain" *Fertility and Sterility*, 63(5):955-962 (1995).
ID W-00200600598, Office Action explanation, Apr. 10, 2012.
JP 2006-525216, Office Action with English translation; Dispatch Date: Oct. 6, 2011.
JP 2006-525216, Office Action with English translation, Jun. 6, 2012.
KR 10-2006-7004304, Office Action with English translation, Aug. 29, 2011.
KR 10-2006-7004304, Office Action translation, May 3, 2012.
Merck Canada Inc., "Prometrium®" Product Monograph. Submission Control No. 145176. Date of Preparation: Feb. 21, 2011, 34 pages.
Obata et al., "Dysmenorrhea" *Nippon Rinsho*, 59(9):1762-1767 (2001).
Soares et al., "Pharmacologic therapies in endometriosis: a systematic review" *Fertility and Sterility*, 98(3):529-555 (2012).
Tavaniotou et al., "Comparison between different routes of progesterone administration as luteal phase support in infertility treatments" *Human Reproduction Update*, 6(2):139-148 (2000).
U.S. Dept. of Health and Human Services, "Endometriosis. Frequently Asked Questions" Updated Nov. 16, 2009, 6 pages.
Extended European Search Report dated May 31, 2013 for European Application No. 13164182.1, 13 pages.
Kopera, Daisy, "Excess Hair Growth," *Handbook of Hair in Health and Disease*, Wageningen Academic Publishers, 2012, 118-136, 19 pages.
Orfanos, C.E., "Androgenetic Alopecia: Clinical Aspects and Treatment," Chapter 19, *Hair and Hair Diseases*, Springer-Verlag Berlin Heidelberg, 1990, 485-527, 43 pages.
Rizwan, Muneeza et al., "Treatment of idiopathic facial hirsutism with medroxyprogesterone acetate iontophoresis," *Journal of Pakistan Association of Dermatologists*, 2009, 19: 90-94, 5 pages.
Simpson, N.B., "The Effect of Drugs on Hair," *Pharmacology of the Skin II*, Springer-Verlag Berlin Heidelberg, 1989, 495-508, 14 pages.
Xu, Mingqiu, "Treatment of Endometrial Cancer with High Dose Progesterone," *Cancer Research on Prevention and Treatment*, 1986, vol. 13, No. 2, 11 pages.
Fraser, Ian, "Current Trends in the Medical Management of Endometriosis," *Indian Obstetrics & Gynaecology*, 6, No. 1, Jan.-Mar. 2016, 10 pages.

\* cited by examiner

METHODS FOR THE TREATMENT OF ENDOMETRIOSIS

RELATED APPLICATIONS

This application claims the benefit of U.S. Provisional Application No. 60/500,217, filed Sep. 3, 2003, and U.S. Provisional Application No. 60/526,355, filed Dec. 1, 2003, both entitled "Methods for the Treatment of Endometriosis". The subject matter of these applications are incorporated herein by reference in their entirety.

FIELD OF THE INVENTION

This invention relates to methods for the treatment of endometriosis and related disorders and conditions.

BACKGROUND

Endometriosis is defined in *The Merck Manual*, 17th edition, Merck & Co., Inc., Whitehouse Station, N.J., USA, chapter 239, as "a nonmalignant disorder in which functioning endometrial tissue is present outside the uterine cavity." It is sometimes referred to as endometriosis externa or adenomyosis externa. Endometriotic tissues contain estrogen and progestogen receptors that enable them to grow and differentiate in response to the changes in hormonal levels during the menstrual cycle. Endometriosis is usually confined to the peritoneal or serosal surfaces of abdominal organs, commonly the ovaries, posterior broad ligament, posterior cul-de-sac, and uterosacral ligaments (sometimes forming uterosacral nodules). Less common sites include the serosal surfaces of the small and large bowel, ureters, bladder, vagina, surgical scars, pleura, and pericardium. Clinical manifestations of endometriosis are pelvic pain, pelvic mass, alteration of menses, and infertility, while lesions on the bowel or bladder may cause pain during defecation or urination, abdominal bloating, and rectal bleeding with menses (most endometriatic implants can bleed during menstruation). Endometriotic implants on the ovary or adnexal structures can form an endometrioma (a cystic mass localized to an ovary) or adnexal adhesions. Endometriosis is reportedly found in 10-15% of women between the ages of 25 and 44 who are actively menstruating, and in 25-50% of infertile women.

Internal endometriosis includes adenomyosis or adenomyoma. Adenomyosis, also referred to as endometriosis interna, is the invasion of endometrial tissue into the muscular tissue (myometrium) of the uterus. If the lesion is generalized the lesion is called adenomyosis and when it is localized to a smaller area of the uterus it is called adenomyoma. It causes symptoms in only a small number of patients, usually late in the reproductive years. Menorrhagia and intermenstrual bleeding are the most common complains, followed by pain, especially menstrual pain, and bladder and rectal pressure. Oral contraceptive steroids and GnRH agonists or antagonists are not regarded as effective, and oral contraceptives may aggravate the symptoms. Only surgery (myomectomy or hysterectomy) is regarded as curative.

Treatments for endometriosis include medical suppression of ovarian function to arrest the growth and activity of endometrial implants, conservative surgical resection of as much endometriotic tissue as possible, a combination of these two treatments, and total hysterectomy, usually with removal of the ovaries and Fallopian tubes. Medical therapy involves estrogen suppression, such as by administration of continuous oral contraception with estrogen/progestogen combination products (with the usual side effects including abdominal swelling, breast tenderness, breakthrough bleeding, and deep vein thrombosis), gonadotropin-releasing hormone (GnRH) agonists or antagonists such as intranasal nafarelin and subcutaneous or depot leuprolide (with the usual side effects including hot flushes, emotional lability, vaginal dryness, and bone demineralization, but the treatment is usually limited to less than six months because of the risk of bone loss), androgens such as oral danazol (with the usual side effects including masculinization effects such as weight gain, acne, and hirsutism, and other side effects including emotional lability, atrophic vaginitis, liver dysfunction, and adverse effects on lipids), and progestogens such as oral and/or intramuscular medroxyprogesterone (with the usual side effects including breakthrough bleeding, weight gain, emotional lability, depression, and atrophic vaginitis).

For example, Lamb, U.S. Pat. No. 4,038,389, discloses an aqueous parenteral formulation of medroxyprogesterone (INN—referred to as medroxyprogesterone acetate) containing a suspension of 200-600 $g \cdot L^{-1}$ of micronized medroxyprogesterone in a mixture of water, sodium sulfate, a quaternary ammonium wetting agent, and glycerol, propylene glycol, polyethylene glycol, or polypropylene glycol, optionally containing a hydrophilic colloid.

Labrie, U.S. Pat. No. 5,362,720, discloses a method for the treatment of breast and endometrial cancer, osteoporosis, and endometriosis by administration of a low dose of a progestogen or other steroid derivative having androgenic activity and low masculinizing activity, for example, medroxyprogesterone. Various routes of administration are suggested, with subcutaneous depot preferred, intending to achieve a serum concentration of <50 $nmol \cdot L^{-1}$, preferably between 1 $nmol \cdot L^{-1}$ and 10, 15 or 25 $nmol \cdot L^{-1}$ depending on the patient response.

Bologna et al., U.S. Pat. No. 5,543,150, discloses a method of progesterone therapy for the prevention of endometrial cancer using relatively low serum progesterone concentrations such as 1-6 $\mu g \cdot L^{-1}$, achieved by vaginal delivery using crosslinked polycarbophil as a vehicle.

International PCT application No. WO 00/15766, U.S. Pat. No. 6,287,602, and US Patent Application Publication No. 2002/0012703, each describe pharmaceutical formulations for treating a cellular proliferative disease (for example, a cancer, including endometrial cancer) comprising a Golgi apparatus disturbing agent, a biocompatible carrier, and a solvent. A Golgi apparatus disturbing agent is brefeldin A and a biocompatible carrier is chitin or chitosan. The formulation can include another active agent, including medroxyprogesterone, and the preferred route of administration is said to be intratumoral or intralesional (defined as an area sufficiently close to a tumor that the active agent exhibits the desired pharmacological activity with respect to the tumor itself).

International PCT publication No. WO 02/28387 and U.S. Patent Application Publication No. 2002/0061303, each disclose a formulation containing a Golgi apparatus disturbing agent (such as the agents described in WO 00/15766) present in an angiogenesis-inhibiting but non-cytotoxic amount, a solvent, and a pharmaceutically acceptable carrier. These are for treating a patient in need of anti-angiogenic therapy.

International PCT publication No. WO 00/21511, discloses the use of subcutaneous progestogens for the treatment of endometriosis. Suitable progestogens are said to include medroxyprogesterone, progesterone, norethisterone, desogestrel, and levonorgestrel.

Ragavan et al., U.S. Pat. No. 6,416,778, describes formulations for regional delivery of drugs, including steroids such as progestins, estrogens, antiestrogens, and antiprogestins, especially micronized danazol in a micro- or nanoparticulate formulation. These formulations can be used for the treatment of endometriosis, endometrial bacterial infections, cancer, and endocrine conditions.

None of these treatments are as effective as desired. Accordingly, there is a need to develop effective medical treatments for endometriosis, including endometriosis externa, endometrioma, adenomyosis, adenomyomas, endometriotic or adenomyotic nodules of the uterosacral ligaments and endometriotic nodules elsewhere such as scar endometriosis. Therefore, among the objects herein, it is an object to provide more effects methods for treatment of endometriosis and compositions therefor.

SUMMARY

Provided are methods for treatment of endometriosis, including endometriosis externa, endometrioma, adenomyosis, adenomyomas, endometriotic or adenomyotic nodules of the uterosacral ligaments and endometriotic nodules elsewhere such as scar endometriosis. In accord with the methods, an effective amount of a progestogen is administered intralesionally.

Thus, endometriosis, including endometriosis externa, endometrioma, adenomyosis, adenomyomas, adenomyotic nodules of the uterosacral ligaments, and endometriotic nodules, such as scar endometriosis are effectively treated by the intralesional administration, including, but are not limited to, transvaginal, endoscopic or open surgical administration including via laparotomy, of a progestogen. Compositions therefor also are provided.

Also provided is a medicament for the treatment of endometriosis, including endometriosis externa, endometrioma, adenomyosis, adenomyomas, adenomyotic nodules of the uterosacral ligaments, and endometriotic nodules elsewhere such as scar endometriosis, by intralesional administration. The medicament is formulated for intralesional delivery and contains a progestogen as an active ingredient. Generally the medicament is a suspension, particularly a non-oil-based suspension, of the active ingredient. Other formulations also are contemplated. The medicament is formulated to increase retention thereof at the site of injection and to minimize any inflammatory response thereto. The formulations also can be used for treatment of fibroids by intralesional administration.

Also provided is a use of a progestogen in the preparation of the medicament for the treatment of endometriosis, including endometriosis externa, endometrioma, adenomyosis, adenomyomas, adenomyotic nodules of the uterosacral ligaments, and endometriotic nodules elsewhere such as scar endometriosis, by intralesional administration.

DETAILED DESCRIPTION

Definitions

Unless defined otherwise, all technical and scientific terms used herein have the same meaning as is commonly understood by one of skill in the art to which the inventions belong. All patents, patent applications, published applications and publications, material on websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

Unless the context clearly dictates otherwise, in this application and its claims, the singular includes the plural. Thus, a reference to a progestogen includes a reference to two or more progestogens, a reference to an excipient includes a reference to two or more excipients, and so forth.

As used herein, "endometriosis" refers to any nonmalignant disorder in which functioning endometrial tissue is present in a location in the body other than the endometrium of the uterus, i.e. outside the uterine cavity or is present within the myometrium of the uterus. For purposes herein it also includes conditions, such as adenomyosis/adenomyoma, that exhibit myometrial tissue in the lesions. Thus the term "endometriosis" includes "endometriosis" as defined in *The Merck Manual*, where the endometrial tissue is present outside the uterine cavity, including uterosacral nodules, endometriomas, adnexal adhesions, and adenomyosis, where the endometrial tissue is present within the myometrium of the uterus.

Endometriosis, as used herein, thus includes the conditions commonly referred to as endometriosis externa (or endometriosis as defined in *The Merck Manual*) endometrioma, adenomyosis, adenomyoma, endometriotic or adenomyotic nodules of the uterosacral ligaments, endometriotic nodules elsewhere such as scar endometriosis, and any nonmalignant disorder in which functioning endometrial tissue is present at a locus other than the endometrium.

As used herein, "endometriotic tissue" is endometrial tissue seen in endometriosis, that is, the endometrial tissue present in a location other than the endometrium of the uterus. Myometrial tissue refers to tissue in the muscle layer of the uterus. This tissue also occurs in lesion treated herein.

As used herein, "treatment" includes one or more of: reducing the frequency and/or severity of symptoms, elimination of symptoms and/or their underlying cause, and improvement or remediation of damage. Thus, treatment of endometriosis includes, for example, relieving the pain experienced by a woman suffering from endometriosis, and/or causing the regression or disappearance of endometriotic lesions.

An "effective amount" of the progestogen means a sufficient amount to effect "treatment" as defined. Treatment can be associated with undesirable effects ("side effects") along with the desired therapeutic effect, so that a medical practitioner prescribing or performing treatment will balance the potential benefits against the potential risks in determining what constitutes an appropriate "effective amount". Also, because the quantity of endometriotic tissue will vary from woman to woman, the "effective amount" of progestogen to be administered can vary. Thus it is not possible to specify an exact "effective amount"; In view of the disclosure herein, however, the skilled medical practitioner, can determine an appropriate "effective amount" in any individual case can be determined.

As used herein, "intralesional administration" means administration into or within a pathological area. Administration is effected by injection into a lesion and/or by instillation into a pre-existing cavity, such as in endometrioma. With reference to treatments for endometriosis provided herein, intralesional administration refers to treatment within endometriotic tissue or a cyst formed by such tissue, such as by injection into a cyst. "Intralesional administration" also includes administration into tissue in such close proximity to the endometriotic tissue such that the progestogen acts directly on the endometriotic tissue, but does not include administration to tissue remote from the endometriotic tissue that the progestogen acts on the endometriotic tissue through systemic circulation. Intralesional administration or delivery includes transvaginal, endoscopic or open surgical administration including, but are not limited to, via laparotomy.

As used herein, transvaginal refers to all procedures, including drug delivery, performed through the vagina, including intravaginal delivery and transvaginal sonography (ultrasonography through the vagina).

As used herein, a subject includes any mammals, typically female mammals, including humans, for whom treatment is contemplated. Subjects also are referred to as patients.

As used herein, formulated for single dosage administration means that a composition can be directly administered without further modification such as dilution.

As used herein, a combination refers to any association between two or among more items.

As used herein, a composition refers to any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination optionally including instructions for use of the combination and/or other reactions and components for such use.

Medicaments

A medicament suitable for use in the methods contains a progestogen as an active ingredient. Typically, it contains a progestogen as the sole active ingredient. The progestogen content of the medicament is such as to provide an effective amount of the progestogen in a quantity of the medicament that is suitable for intralesional administration; for example, a concentration of the progestogen of 1-50% weight/volume, for example 5-25, e.g. about 5-20%, such as 10%, weight/volume. The progestogen will be reduced to a particle size suitable for intralesional administration by injection. If the progestogen is to be administered in a medicament in which it is a solution or suspension, the progestogen will desirably be micronized, for example reduced to a fineness such that 99 wt. % has a particle size less than 10 μm and 75 wt. % has a particle size less than 5 μm. Micronized particles can be of any suitable size, including greater than 10 μm and can be up to a particle size of 100 μm.

The progestogen, for example, can be one or more of progesterone, desogestrel, etonogestrel, gestodene, levonorgestrel, medroxyprogesterone, norethisterone, norgestimate and norgestrel. The amount of progestogen administered per lesion typically is equivalent in activity to 0.2-5 g of progesterone, such as 1-2 g, of progesterone.

Suitable excipients are well known and include, but are not limited to, aqueous (or water-miscible) and nonaqueous solvents. A typical nonaqueous solution medicament is prepared by mixing the solvents, dissolving the remaining excipients and the progestogen in the solvent mixture, sterilizing and filtering the resulting solution, and filing into sterile containers.

Existing injectable preparations of progestogens, such as progesterone, are oil based and cannot be injected into reproductive tract tissue. The formulations provided herein are not oil based so that they avoid the inflammatory process associated with oil preparations. Also, included are formulations that contain suspensions of microparticles that increase the local tissue drug concentrations.

Solvents for the medicaments include, but are not limited to, water, $C_{2-6}$ alkanols, diols and polyols such as, for example, propylene glycol, glycerol, polyethylene glycol, and polypropylene glycol. Excipients include, but are not limited to, solubility enhancers, which can include the alkanols, diols, and polyols mentioned above; buffers such as acetate, citrate, and phosphate acid/salt combinations; wetting agents (surfactants) such as quaternary ammonium salts, polyoxyethylene ethers such as the octoxynols, polysorbates, polyoxyethylated sorbitan esters, and other anionic, nonionic, and cationic surfactants; chelating agents such as edetate disodium and other edetate salts; antioxidants such as ascorbic acid and its salts and esters, BHA, BHT, sulfite and bisulfite salts, tocopherol and its esters; antimicrobial agents such as, but not limited to, chlorobutanol, the parabens and their salts and esters, thimerosal, benzethonium chloride, benzalkonium chloride; tonicifiers, such as electrolytes, e.g. sodium chloride, and mono- and di-saccharides, such as, for example dextrose.

Medicaments, including aqueous medicaments, also can contain viscosity increasing and suspending agents such as hydrophilic colloids, e.g. dextran, gelatin, hydroxyethylcellulose, methylcellulose, polyvinyl alcohol and povidone, and ionic hydrophilic colloids such as sodium carboxymethylcellulose. Nonaqueous medicaments can completely dissolve the progestogen; but if they do not, they also can contain viscosity increasing and suspending agents. Further guidance to suitable excipients and their formulation are known to those of skill in the art (see, e.g., standard pharmaceutical references such as "Remington: The Science and Practice of Pharmacy", 20th edition, A. Gennaro, ed., Lippincott, Williams & Wilkins, Philadelphia, USA).

A typical suspension medicament, such as, for example, an aqueous suspension, is prepared by mixing the solvents, dissolving the remaining excipients in the solvent mixture, sterilizing the resulting solution (such as by sterile filtration), adding the already-sterilized progestogen, milling and/or mixing the resulting suspension to uniformity, sterilizing the suspension (such as by heat or filtration), filtering if necessary, and filling into sterile containers, typically of a volume between 1 and 10 mL. The medicament can be formulated for direct (single dosage) administration or can be formulated for dilution in carrier prior to administration.

Although any progestogen containing medicament suitable for intralesional administration can be employed in the methods herein, particular medicaments also are provided herein. These medicaments are formulated as suspensions, typically micronized suspensions, with a progestogen at a concentration to deliver about 0.2-5 g of progesterone, such as 1-2 g, of progesterone per dosage to a lesion at a concentration of 1-50% weight/volume. An exemplary suspension medicament provided herein is described in Example 1 below.

The medicaments can be packaged as articles of manufacture containing packaging material, a medicament of the present invention formulated for single dosage administration for intralesional administration for treatment of endometriosis, and a label that indicates that the medicament is for treatment of endometriosis by intralesional administration.

Combinations of the medicament and one or more needles are provided. Also provided are kits for practice of the methods herein. The kits contain one or more containers, such as sealed vials, with sufficient medicament composition for single dosage administration, and one or more needles, such as 20 gauge needles, suitable for intralesional injection for treatment of endometriosis. The formulation can be provided, for example, in a container, such as an ampoule or vial. The kit can contain a separate syringe and needle or a preloaded. The kit also can contain sterile water for dilution of the formulation as needed depending on the size of the lesion as well as other parameters.

Methods of Treatment

The method of treatment of endometriosis provided herein employs intralesional administration of the progestogen formulated as a medicament, particularly a non-oil based formulation. Administration is by injection into the endometriotic tissue or into a cyst formed by such tissue; or into tissue immediately surrounding the endometriotic tissue in such proximity that the progestogen acts directly on the endometriotic tissue.

Typically, the tissue is visualized, for example laparoscopically or by ultrasound, and the progestogen is administered by intralesional (intracystic) injection by, for example direct visualization under ultrasound guidance or by any other suitable methods. A suitable amount of the progestrogen expressed in terms of progestrone of about 1-2 gm per lesion/cyst can be applied. Precise quantity generally is determined on case to case basis, depending upon parameters, such as the size of the endometriotic tissue mass, the mode of the administration, and the number and time intervals between treatments. For other progestrogens the amount should be equivalent to that of a quantity of progestrone, which, if necessary can be assayed in vitro and/or in vivo. Progestrone can be assayed as per different pharmacopea like USP/NF/BP/IP etc as applicable to different countries.

Delivery

As noted the methods herein employ intralesional delivery of the medicaments into the lesion. Intralesional delivery includes, for example, transvaginal, endoscopic or open surgical administration including via laparotomy. Delivery can be effected, for example, through a needle or needle like device by injection or a similar injectable or syringe-like device that can be delivered into the lesion, such as transvaginally, endoscopically or by open surgical administration including via laparotomy.

In practicing the methods delivery can be combined with aspiration of the contents of the lesion. For example, delivery includes intravaginal and transvaginal delivery. For intravaginal/transvaginal delivery an ultrasound probe can be used to guide delivery of the needle from the vagina into lesions such as endometriomas and utero sacral nodules. Under ultrasound guidance the needle tip is placed in the lesion, the contents of the lesion aspirated if necessary and the formulation is injected into the lesion.

Delivery System

In an exemplary delivery system a 17 to 20 gauge needle can be used for injection of the drug. Such system can be used for intralesional delivery including, but not limited to, transvaginal, endoscopic or open surgical administration including via laparotomy. For treatment of endometrioma 17 or 18 gauge needles are used under ultrasound guidance for aspiration of the thick contents of the lesion and delivery of the formulation. The length of the needle used depends on the depth of the lesion. Pre-loaded syringes and other administration systems, which obviate the need for reloading the drug can be used.

The following examples are included for illustrative purposes only and are not intended to limit the scope of the invention.

Example 1

Manufacture of a Suspension Medicament Comprising Progesterone

Under aseptic conditions and at about 22° C., polyethylene glycol 400 (100 ml) was dissolved in water with stirring. To the resulting solution was added, in order and with stirring, 10 gm sodium carboxymethylcellulose, 0.1 gm methyl paraben, 0.1 gm propyl paraben, and 1 ml polysorbate 80 (Tween 80). Micronized progesterone (40 g; sterile) was added and the mixture stirred until a uniform suspension had been achieved. The suspension was sterilized by autoclaving, then filtered to ensure uniform suspension, and aliquots filled into vials, which were sealed under aseptic conditions. The final formulation was a white suspension containing 100 mg/mL progesterone, having a pH between 4 and 7.5 and viscosity of 53-60 cP, readily capable of injection through a standard 17 gauge to 20 gauge needle. The suspension was uniform and stable on storage without any precipitation.

Example 2

Young Woman with Proven Grade 4 Endometriosis and Previous History of Two Pelvic Surgeries Presenting with Recurrent Bilateral Ovarian Endometrioma, Infertility and Severe Pelvic Pain A 28 year old woman was complaining of severe pelvic pain, dysmenorrhea, and infertility of three years duration was seen. She had had a laparoscopic procedure a year previously for management of similar complaints. Grade 4 endometriosis, bilateral ovarian endometrioma of 5 to 6 cm, obliterated POD, peritubal and paraovarian adhesions were noted and treated at that time. Because of persistence of lesions she was started on oral danazol 800 mg per day for four months. This was followed by pelvic reconstructive surgery six months after the laparoscopy. Laparotomy, bilateral ovarian cyst resection and adhesiolysis were carried out. She had several cycles of ovulation induction and fertility management following the surgery, without any success.

Her symptoms reoccurred. Physical examination followed by ultrasound assessment confirmed the presence of recurrent endometriotic cysts, 4 cm in the right and 5 cm in the left ovary.

Under ultrasound guidance, the cysts were aspirated with an 18 gauge needle. 25 cc of chocolate colored fluid was aspirated. A saline wash was given and 2 g of progesterone in the suspension of Example 1 was instilled into each cyst. She was regularly monitored by pain scores (visual analog), direct questionnaire, and ultrasound examination. At the end of 12 weeks both ovaries were normal on ultrasound examination and she was pain free. She underwent 2 cycles of superovulation and IUI. She conceived in the second treatment cycle and the pregnancy proceeded.

Example 3

41 Year Old with Symptomatic Grade 4 Endometriosis and Uterosacral Adenomyotic Nodule A 41 year old nulliparous woman had been diagnosed with endometriosis several years earlier. She had a laparotomy in 1990 when grade 4 endometriosis was diagnosed. Pelvic reconstructive surgery was done at that time. Subsequently she had undergone repeated attempts at medical treatment with oral contraceptives, danazol, and depot GNRH analogs. She also had an unsuccessful IVF attempt. The patient presented with a request for hysterectomy as the quality of her life was disturbed due to severe pelvic and rectal pain.

Physical examination and ultrasound assessment revealed that she had a right sided ovarian endometrioma, fixed uterus, tender left ovary and uterosacral adenomyotic nodules. Ultrasound guided transvaginal aspiration of the endometrioma was done. Two grams of progesterone in the suspension of Example 1 was instilled into the endometrioma and the adenomyotic nodule was injected. She reported improvement in pelvic pain within 10 days. On subsequent follow up visits during the following 15 months, there was no recurrence of symptoms. Her quality of life with regard to dysmenorrhea, dyspareunia and pelvic pain improved significantly and she has not required any invasive surgery.

Example 4

A 37 Year Old with Ovarian, Urinary Bladder and Scar Endometriosis

A 37 year old multiparous woman underwent lower segment Caesarian section in 1987 for obstetric reasons. She presented with a mass lesion in the scar in 1995. The lesion was excised and proved to be scar endometriosis. Subsequently in 2000 she developed chronic pelvic pain and urinary symptoms. Physical examination, ultra sonography and cystoscopy revealed right ovarian endometrioma and endometriotic nodules in the bladder wall close to the scar.

Aspiration of the endometrioma and intracystic instillation of 1 g of progesterone was performed. Cystoscopy was carried out and 1 g of progesterone was instilled in each of the nodules in the bladder.

On follow up for over 12 months she has remained symptom free. Quality of life with regard to pelvic pain and urinary symptoms has been good. Major pelvic surgery, i.e. total abdominal hysterectomy, bilateral salpingo-oopherectomy, bladder wall excision and reconstruction, has been averted.

Example 5

43 Year Old Perimenopausal Woman with Endometrioma, Adenomyosis Uteri and Pelvic Pain In September 2001, a 43 year old multiparous woman presented had complaints of severe pelvic pain, left lower abdominal pain and severe dysmenorrhea. The pain was not relieved by regular analgesics and anti spasmodics. Examination and ultrasonography revealed an adenomyotic uterus and left ovarian endometrioma. The patient had been counseled to have a total abdominal hysterectomy, but she requested conservative management and wished to avoid the possibility of surgery and losing her ovaries.

Transvaginal aspiration of the endometrioma was done, and 2 g of progesterone in the suspension of Example 1 was instilled into the cavity. This was followed by intravaginal micronized progesterone for 8 weeks. The patient retained her ovaries and has remained symptom free for nearly 2 years.

Since modifications will be apparent to those of skill in this art, it is intended that this invention be limited only by the scope of the appended claims.

The invention claimed is:

1. A dosage unit comprising a micronized progestogen in an amount equivalent to 1.0-5.0 g of progesterone in a non-oil based suspension formulated for intralesional injection into an endometriotic lesion or fibroid, wherein the unit dosage is formulated with at least one viscosity increasing/suspending agent for increased retention at the site of injection.

2. The dosage unit according to claim 1, wherein the progestogen is in an amount equivalent to 1-2 g of progesterone.

3. The dosage unit according to claim 1, wherein the progestogen is selected from the group consisting of progesterone, desogestrel, etonogestrel, gestodene, levonorgestrel, medroxyprogesterone, norethisterone, norgestimate, and norgestrel.

4. The dosage unit according to claim 1, wherein the progestogen is progesterone.

5. The dosage unit according to claim 1, wherein the progestogen is micronized to a particle size of less than or equal to 100 μm.

6. The dosage unit according to claim 1, wherein the progestogen is micronized to a particle size of greater than 10 μm.

7. The dosage unit according to claim 1, wherein the viscosity is 53-60 cP.

8. The dosage unit according to claim 1, wherein the pH is between 4 and 7.5.

9. The dosage unit according to claim 1, wherein the progestogen is 1-50% weight/volume.

10. The dosage unit according to claim 9, wherein the progestogen is 5-20% weight/volume.

11. The dosage unit according to claim 9, wherein the progestogen is 10% weight/volume.

12. The dosage unit of claim 1, wherein 99 wt. % of the progestogen has a particle size less than 10 μm and 75 wt. % of the progestogen has a particle size less than 5 μm.

13. The dosage unit of claim 12, wherein the viscosity is 53-60 cP.

14. A pharmaceutical composition formulated for intralesional injection into an endometriotic lesion or fibroid comprising a micronized progestogen in an amount equivalent to 1.0-5.0 g of progesterone per lesion in a non-oil based suspension; wherein the unit dosage is formulated with at least one viscosity increasing/suspending agent for increased retention at the site of injection and at least one excipient.

15. The pharmaceutical composition according to claim 14, wherein the progestogen is in an amount equivalent to 1-2 g of progesterone per lesion.

16. The pharmaceutical composition according to claim 14, wherein the progestogen is selected from the group consisting of progesterone, desogestrel, etonogestrel, gestodene, levonorgestrel, medroxyprogesterone, norethisterone, norgestimate, and norgestrel.

17. The pharmaceutical composition according to claim 14, wherein the progestogen is progesterone.

18. The pharmaceutical composition according to claim 14, wherein the progestogen is micronized to a particle size of less than or equal to 100 μm.

19. The pharmaceutical composition according to claim 14, wherein the progestogen is micronized to a particle size of greater than 10 μm.

20. The pharmaceutical composition according to claim 14, wherein the viscosity is 53-60 cP.

21. The pharmaceutical composition according to claim 14, wherein the pH is between 4 and 7.5.

22. The pharmaceutical composition according to claim 14, wherein the progestogen is 1-50% weight/volume.

23. The pharmaceutical composition according to claim 22, wherein the progestogen is 5-20% weight/volume.

24. The pharmaceutical composition according to claim 22, wherein the progestogen is 10% weight/volume.

25. A kit comprising a dosage unit according to claim 1 or a pharmaceutical composition according to claim 14 and a needle.

26. The kit according to claim 25, further comprising instructions for intralesional administration of the dosage unit or pharmaceutical composition.

27. The kit according to claim 25, wherein the dosage unit or pharmaceutical composition comprises a progestogen in an amount equivalent to 1-2 g of progesterone per lesion.

28. The kit according to claim 25, wherein the progestogen in the dosage unit or pharmaceutical composition is selected from the group consisting of progesterone, desogestrel, etonogestrel, gestodene, levonorgestrel, medroxyprogesterone, norethisterone, norgestimate, and norgestrel.

29. The kit according to claim 28, wherein the progestogen in the dosage unit or pharmaceutical composition is progesterone.

30. The kit according to claim 25, wherein the progestogen in the dosage unit or pharmaceutical composition is micronized to a particle size of less than or equal to 100 μm.

31. The kit according to claim 25, wherein the progestogen in the dosage unit or pharmaceutical composition is micronized to a particle size of greater than 10 μm.

32. The kit according to claim 25, wherein the viscosity of the dosage unit or pharmaceutical composition is 53-60 cP.

33. The kit according to claim 25, wherein the pH of the dosage unit or pharmaceutical composition is between 4 and 7.5.

34. The kit according to claim 25, wherein the progestogen in the dosage unit or pharmaceutical composition is 1-50% weight/volume.

35. The kit according to claim 34, wherein the progestogen in the dosage unit or pharmaceutical composition is 5-20% weight/volume.

36. The kit according to claim 34, wherein the progestogen in the dosage unit or pharmaceutical composition is 10% weight/volume.

37. The pharmaceutical composition of claim 14, wherein 99 wt. % of the progestogen has a particle size less than 10 μm and 75 wt. % of the progestogen has a particle size less than 5 μm.

38. The pharmaceutical composition of claim 37, wherein the viscosity is 53-60 cP.

39. A dosage unit comprising a micronized progestogen in an amount equivalent to 1.0-5.0 g of progesterone in a non-oil based suspension formulated for intralesional injection into an endometriotic lesion or fibroid, wherein the unit dosage is formulated with a hydrophilic colloid to increase retention to the site of injection.

40. The dosage unit of claim 39, wherein 99 wt. % of the progestogen has a particle size less than 10 μm and 75 wt % of the progestogen has a particle size less than 5 μm.

41. The dosage unit of claim 40, wherein hydrophilic colloid is carboxymethyl cellulose.

42. The dosage unit of claim 41, wherein the viscosity is 53-60 cP.

* * * * *